United States Patent [19]  [11] 4,396,528
Abbott  [45] Aug. 2, 1983

[54] FLUORESCENT COMPOSITION, A PROCESS FOR SYNTHESIZING THE FLUORESCENT COMPOSITION

[75] Inventor: Seth R. Abbott, Concord, Calif.

[73] Assignee: Varian Associates, Inc., Palo Alto, Calif.

[21] Appl. No.: 271,861

[22] Filed: Jun. 9, 1981

Related U.S. Application Data

[62] Division of Ser. No. 953,380, Oct. 23, 1978, Pat. No. 4,275,000.

[51] Int. Cl.$^3$ .................... C09K 11/06; C09K 11/20
[52] U.S. Cl. ............................................. 252/301.17
[58] Field of Search ..................... 252/301.16, 301.17

[56] References Cited

U.S. PATENT DOCUMENTS

| | | | |
|---|---|---|---|
| 2,935,481 | 5/1960 | Hochwalt | 252/301.16 |
| 3,150,101 | 9/1964 | Heimbuch | 252/301.17 |
| 3,314,894 | 4/1967 | Nyilas et al. | 252/301.17 |
| 3,513,102 | 5/1970 | Heidke | 252/301.16 X |
| 3,666,683 | 5/1972 | Maeder et al. | 252/408 |
| 3,904,373 | 9/1975 | Harper | 422/57 |
| 3,930,063 | 12/1975 | Miller et al. | 427/54 |
| 4,043,905 | 8/1977 | Novotny et al. | 210/31 |
| 4,275,300 | 6/1981 | Abbott | 250/304 |

OTHER PUBLICATIONS

Locke et al., *Analytical Chemistry*, vol. 44, No. 1, pp. 90–92, (Jan. 1972).
Clifford et al., *Journal of Chromatography*, vol. 40, pp. 377–385, (1969).
Sieswerda et al., *Journal of Radioanalytical Chemistry*, vol. 11, pp. 49–58, (1972).
M. A. Crook et al., ed. *Liquid Scintillation Counting*, vol. 2, Chapter 4, by Sieswerda and Polak, Heyden Publishing Co., (1972).
Schutte, *Journal of Chromatography*, vol. 72, pp. 303–309, (1972).
Asmus et al., *Journal of Chromatography*, vol. 126, p. 317, (1976).

*Primary Examiner*—F. Edmundson
*Attorney, Agent, or Firm*—Stanley Z. Cole; Norman E. Reitz

[57] ABSTRACT

A fluorescent composition useful in thin-layer chromatography comprises an inert porous particle having a fluorescent material fixedly attached by covalent chemical bonding to the surface thereof. A process for synthesizing this fluorescent composition is disclosed. A method for detecting the radioactivity of a radioactive species using a cell packed with such a fluorescent composition is also disclosed.

27 Claims, No Drawings

FLUORESCENT COMPOSITION, A PROCESS FOR SYNTHESIZING THE FLUORESCENT COMPOSITION

This is a division of application Ser. No. 953,380 filed Oct. 23, 1978 now U.S. Pat. No. 4,275,000 issued June 23, 1981.

BACKGROUND OF THE INVENTION

Fluorescent Composition

Compositions in which a particle (such as a hydrophobic silica aerogel) is coated with a fluorescent material are known. As an example of this type of prior art, U.S. Pat. No. 2,935,481 to Hochwalt discloses use of a hydrophobic silica as a carrier for a water-soluble fluorescent dye that may be present as a mere surface coating or as an absorbed or adsorbed coating. The fluorescent dye of Hochwalt is releasably coated onto the silica, whereby the dye is released when the coated silica is placed in an aqueous solution.

It was also known to the prior art to use an organic scintillator in a radiation-sensitive layer in a radiation-sensitive recording element, as exemplified by the disclosure in U.S. Pat. No. 3,513,102 to Heidke. In this type of prior art, the organic scintillator is dissolved along with a solid-solution carrier (such as a water-insoluble resin) in a solvent, and the resulting solution is dispersed in an aqueous solution of a hydrophilic colloid prior to coating the dispersion onto a substrate so as to form a radiation-sensitive layer.

It was also known to the prior art to produce a plastic phosphor bead having a cross-linked polymer matrix (such as polyvinyltoluene cross-linked with divinylbenzene), with the fluorescent material being dissolved in solid solution within the bead. Illustrative of this type of prior art is U.S. Pat. No. 3,150,101 to Heimbuch.

Highly fluorescent organic compounds (i.e., highly fluorescent materials) are well known in the art, as exemplified by U.S. Pat. Nos. 3,666,683 and 3,314,894 and by the patents to Heidke and Heimbuch discussed above. U.S. Pat. No. 3,930,063 to Miller et al. discloses mixing together a silica salt having large particle size and a fluorescent dye.

It was known to the prior art to affix an alkyl or aryl substituent to the surface of siliceous materials by covalent chemical bonding with the resultant bonded materials being used for chromatography. Exemplary of this type of prior art is Locke et al., *Analytical Chemistry*, Vol. 44, No. 1, pages 90–92 (January 1972). It was also known to react a siliceous surface with monohalogenated silanes, silazanes or silylamines, or with monoalkoxy or monoacetoxysilanes, and then to cause a chemical modification of the reaction product. Such reaction products are useful for high-resolution chromatography. This type of prior art is illustrated by U.S. Pat. No. 4,043,905 to Novotny et al.

The prior art discussed above is pertinent with respect to the fluorescent composition of the present invention. However, none of this prior art discloses a composition comprising an inert porous particle to which a highly fluorescent material is fixedly attached by covalent chemical bonding.

Methods of Using the Fluorescent Composition

It was known to the prior art to pass the effluent from a chromatographic column through a flow cell packed with beads of a lithium-cerium glass, and then to monitor radioactivity. This technique was discussed by Clifford et al. in *Journal of Chromatography*, Vol. 40, pages 377–385 (1969). A shortcoming of this technique is that ionic compounds contained in the effluent are adsorbed onto the negatively-charged glass surface, which leads eventually to clogging of the flow cell and increasing radioactive background. Also, glass is slightly soluble in pH 2 to 8 water, with solubility rapidly increasing above pH 8. Furthermore, a cerium glass scintillator has a very long-lived phosphorescence that is activated by ambient light; thus, once the flow cell has been activated by room light, several days are required for the cell background to decay to a usable level. Significantly, the glass beads used in the technique described by Clifford et al. are not microparticulate, and therefore tend to cause band broadening of the chromatographic column peaks.

Other prior art relates to the use of a flow cell packed with a solid scintillator such as anthracene. Illustrative of this type of prior art is the publication by Sieswerda et al. in *Journal of Radioanalytical Chemistry*, Vol. 11, pages 49–58 (1972). Related to this Sieswerda et al. publication is chapter 4 of a book edited by M. A. Crook et al, entitled *Liquid Scintillation Counting*, Volume 2, Heyden Publishing Co., 1972, which chapter was written by Sieswerda and Polak. Also illustrative of the use of glass scintillator beads is Schutte, *Journal of Chromatography*, Vol. 72, pages 303–309 (1972).

It was also known in the prior art to pass the effluent from a chromatographic column through an open tube, i.e., an unpacked flow cell. In using this approach, a "scintillation cocktail" is added to the column effluent after the effluent has passed from the column and before it enters the flow cell. When the column effluent is aqueous, it is necessary that 5 to 10 volumes of scintillation cocktail be added for each volume of column effluent in order to counteract the diluent effect of the aqueous solvent upon the scintillation process and to prevent aqueous precipitation of the scintillator. As a result of the addition of this large quantity of scintillation cocktail to the effluent, the flow rate through the open flow cell is increased, thereby causing laminar flow band broadening and reduced resolution. Another disadvantage of this technique is that a pump must be used to deliver the scintillation cocktail to the column effluent, thereby complicating and adding to the cost of the apparatus necessary for the performance of this technique. Also, the need to supply a high excess of scintillation cocktail is economically disadvantageous, since the scintillation cocktail is costly.

The prior art does not disclose a method for detecting a radioactive species in the effluent from a chromatographic column by passing the effluent through a flow cell that is packed with a fluorescent composition comprising inert porous particles to the surface of which a highly fluorescent material has been attached by covalent chemical bonding. Furthermore, the prior art does not disclose the use of such a composition for detecting a nonfluorescent species, or the use of such a composition in thin-layer chromatography.

SUMMARY OF THE INVENTION

An object of the present invention is to provide a novel fluorescent composition comprising an inert porous particle to the surface of which a highly fluorescent material is attached by covalent chemical bonding.

Another object of the present invention is to provide a process for producing this fluorescent composition.

A further object of the present invention is to provide a novel method for detecting radioactivity by using this fluorescent composition packed in a cell.

A more particular object of this invention is to provide a method for continuous radioactivity detection in a high-pressure liquid chromatography system.

Another particular object of this invention is to provide a novel method for detecting a nonfluorescent species.

An additional object of this invention is to provide a novel method for the thin-layer chromatography of a radioactive species using a fluorescent composition comprising an inert porous particle to the surface of which a highly fluorescent material is attached by covalent chemical bonding.

Other objects and advantages of the present invention can be ascertained from a perusal of the following description.

To accomplish the foregoing objects, this invention provides a fluorescent composition comprising an inert porous particle having a maximum cross-sectional dimension in the range from about 5 to 20 microns with a highly fluorescent material covalently bonded to the surface thereof.

This invention also provides a process for the manufacture of such a fluorescent composition, wherein the inert porous particle is microparticulate silica. The manufacturing process for this fluorescent composition includes the steps of:

(a) reacting an amine linking agent with an aqueous slurry of the silica, whereby an intermediate product is formed consisting of the amine linking agent covalently bonded to the silica;

(b) recovering, washing and drying the intermediate product;

(c) reacting a slurry of the dried intermediate product with the fluorescent material, whereby the fluorescent composition is produced; and (d) recovering, washing and drying the fluorescent composition.

Also, according to the present invention, a method is provided for detecting the radioactivity of a radioactive species. This method includes the steps of (a) placing the radioactive species in a cell packed with the fluorescent composition; and (b) detecting the emitted radioactivity. When the radioactivity being detected by the method of this invention is that of tritiated hydrogen or carbon-14, the fluorescent composition has a particle of a size of about 5-10 microns.

Also provided by the present invention is a method for detecting a nonfluorescent species. This method includes the steps of (a) irradiating a cell, which has been packed with the fluorescent composition, with electromagnetic radiation of a frequency that causes the fluorescent composition to fluoresce; and detecting the emitted fluorescence;

(b) continuing said irradiation and detection, while placing the nonfluorescent species in the cell; and (c) detecting either an enhancement or reduction in intensity, or a shift in frequency of the emitted fluorescence due to the presence of the nonfluorescent species.

The present invention also provides a method for accomplishing a thin-layer chromatographic analysis of a radioactive species, wherein the improvement includes performing the chromatographic analysis on a substrate onto which the fluorescent composition has been coated.

BEST MODE FOR PRACTICING THE INVENTION

Fluorescent Composition

The fluorescent composition of this invention comprises an inert porous particle to the surface of which is attached a highly fluorescent material by covalent chemical bonding. The particle has a size in the range from about 5 to 20 microns, with a size in the range from about 5 to 10 microns being preferred.

The particle must be inert, i.e., it must be highly stable in organic solvents and in aqueous buffer solutions of about pH 2 to 8 at ambient temperature. Exemplary organic solvents in which the particle must be highly stable are hexane, heptane, isooctane, cyclohexane, ether, dichloromethane, chloroform, methanol, isopropanol, ethanol, acetonitrile and tetrahydrofuran.

A particle that meets the above requirements may suitably be composed of microparticulate silica, alumina, a cross-linked dextran, or a cross-linked polystyrenedivinylbenzene resin. Preferably, the particle is composed of microparticulate silica or alumina, since the dextran and the polystyrene-divinylbenzene resin tend to shrink or swell with solvent changes. Microparticulate silica is especially preferred, and a high-pressure liquid chromatography (HPLC) grade silica gel is a particularly suitable type of this silica. An HPLC grade silica gel having a high surface area, i.e., about 200 to 800 $m^2/g$, and a size of about 5 to 10 microns is an especially suitable type of silica gel. Such a silica gel is commercially available as 10-micron Lichrosorb®  Si-60, sold by Merck, Inc. However, any chromatography grade silica gel would be suitable.

Microparticulate silica can be used in an aqueous buffer solution of about pH 1 to 8, alumina can be used in an aqueous buffer solution of about pH 1 to 10, a cross-linked dextran can be used in an aqueous buffer solution of about pH 2 to 12, and a cross-linked polystyrene-divinylbenzene resin can be used in an aqueous buffer solution of any pH. Microparticulate silica, alumina, cross-linked dextrans and cross-linked polystyrene-divinylbenzene resins are generally well known to those skilled in the art.

The highly fluorescent material that is fixedly attached to the particle may be any highly fluorescent material, with the only limitation being that the fluorescent material must be capable of being fixedly attached by covalent chemical bonding to the particle. Exemplary fluorescent materials of this type are dansyl chloride (also known as N,N-dimethylamionaphthylsulfonyl chloride), dansyl hydrazine, dansyl aziridine, fluorescamine (also known as Fluram®, sold by Hoffman LaRoche), bansyl chloride, and 4-(N,N-dimethylamine)-1-naphthylisothiocyanate. Dansyl chloride is particularly suitable for use in this invention.

It is necessary that the fluorescent material be fixedly attached to the surface of the particle by covalent chemical bonding. Accordingly, a particle of the type described above that is merely coated with a fluorescent material of the type described above is not within the scope of the present invention. As discussed more fully below, the fluorescent composition of the present invention, when packed in a cell, is useful for detecting radioactivity and for detecting certain nonfluorescent species; and in thin-layer chromatography the fluorescent composition of this invention acts as the chromatographic medium and permits detection of radioactive bands. In contrast, a coated particle would be useless for these applications.

In one embodiment of the fluorescent composition of the present invention, the fluorescent material is fixedly attached to microparticulate silica through the intermediacy of an amine linking agent that acts to link the fluorescent material and the silica. Exemplary amine linking agents are a primary or secondary amine-containing mono-, di-, or trialkoxysilane. Other linking agents are an aldehyde- or ketone-containing mono-, di-, or trichloro or trialkoxysilane; a thiol-containing mono-, di-, or trialkoxysilane; and a blocked phenol-containing mono-, di-, or trialkoxysilane. A suitable amine-containing alkoxysilane is N-2-aminoethyl-3-aminopropyl trimethoxysilane (AEAPS). A suitable thiol-containing alkoxysilane in 3-mercaptopropyl trimethoxysilane. When an amine-containing alkoxysilane is selected, suitable fluorescent materials are dansyl chloride, fluorescamine, bansyl chloride and 4-(N,N-dimethylamino)-1-naphthylisothiocyanate. When an aldehyde or ketone-containing alkoxy- or chloro-silane is selected, a suitable fluorescent material is dansyl hydrazine. When a thiol-containing alkoxysilane is selected, a suitable fluorescent material is dansyl aziridine. When a blocked phenol-containing alkoxysilane is selected, dansyl chloride is suitable as the fluorescent material, although it is necessary to unblock the phenol group prior to reaction with the dansyl chloride. When dansyl chloride is selected as the fluorescent material, the fluorescent composition produced from the silica and AEAPS is didansyl-N-2-aminoethyl-3-aminopropyl silica. Thus, depending upon the linking agent and the fluorescent material selected, numerous silicas can be provided that are within the scope of this invention.

In the preferred silica-containing fluorescent composition, the relatively hydrophobic organic outer portion of the composition provides protection to the silica inner portion against gradual attack by an aqueous solvent by shielding the silica from the aqueous solvent. This shielding effect exists regardless of the type of particle selected, but is more important for certain of the particle types such as silica. Also, with this preferred silica-containing embodiment of the fluorescent composition, negatively charged and polar silanol groups are eliminated from the silica surface by tying these groups up in a covalent bond. The elimination of these disadvantages associated with silica avoids the adsorption and clogging problems experienced with prior art compositions (such as Ce-activated glass scintillators) when the silica-containing fluorescent composition of the present invention is used for radioactivity detection as described below.

Method of Manufacture

The present invention also provides a process for the manufacture of a fluorescent composition having microparticulate silica of the type described above as the particle. Preferably, this silica is a high-pressure liquid chromatography grade silica gel, and preferably this silica has a size of about 5 to 10 microns. An especially suitable type of HPLC grade silica gel has a high surface area, i.e., about 200 to 800 $m^2/g$, and a size of about 5 to 10 microns. A suitable commercially available silica gel for this purpose is 10-microns Lichrosorb ® Si-60, sold by Merck. However, the silica may be any chromatography grade silica gel.

In the first essential step of this process, an amine linking agent of the type disclosed above is reacted with an aqueous slurry of the silica. This reaction is conducted for a time and at a temperature sufficient to produce an intermediate product consisting of the amine linking agent covalently bonded to the silica. A sufficient time and temperature would be 2 to 4 hours at room temperature. Suitably, the reaction is carried out at about room temperature for about 3 hours. In preparing the aqueous slurry of the silica to which the amine linking agent is suitably added, an amount of silica needed to form an about 10% by weight slurry is advantageously added to water. An excess of amine linking agent to reactive silanol sites on the silica is suitably used, with an about two-fold excess being preferred.

As the next essential step of this process, the intermediate product is recovered, washed and dried. Recovery is advantageously carried out by filtering the resulting reaction slurry of the preceding essential step. Suitably, the slurry is filtered through a sintered glass filter funnel having a pore size smaller than the particle size, and the intermediate product is recovered as a filter cake. The filter cake is washed using a series of solvents to remove solvent-soluble impurities. An advantageous series of solvents comprises water, methanol, tetrahydrofuran and then methanol again. About 250 milliliters of each of these solvents are suitably used in the washing. Then, the filter cake is dried according to conventional procedures.

Next, the dried intermediate product is reacted with a fluorescent material of the type disclosed earlier so as to produce the fluorescent composition of the present invention. In carrying out this reaction, the fluorescent material (e.g., dansyl chloride) is suitably added to a slurry of the intermediate product in a mixture of a water-miscible organic solvent and a saturated (e.g., with sodium bicarbonate) aqueous solution. The organic solvent is advantageously present in excess or in an about stoichiometrically equal amount with respect to the aqueous solution, with a ratio in the range of about 9:1 to 1:1 being illustrative. An about 4:1 ratio is preferred. The critical factor in selecting the ratio is the solubility of the fluorescent material in the saturated aqueous solution. Illustrative water-miscible organic solvents are acetonitrile, acetone and tetrahydrofuran. Acetonitrile is a preferred organic solvent. In forming the saturated aqueous solution, an inorganic salt is used with a preferred salt providing a solution buffered to a pH of about 8.3, which is the optimum pH for the reaction. The aqueous solution is suitably water saturated with sodium bicarbonate as the inorganic salt.

In preparing the slurry to which the intermediate product is suitably added, there is added to the solvent mixture an amount of the intermediate product that will form about a 10% by weight slurry. The reaction is carried out at a temperature and for a time sufficient to produce a fluorescent composition wherein the intermediate product is covalently bonded to the fluorescent material. A sufficient temperature and time would be about 40° to 60° C. for about 1 to 3 hours, with a reaction condition of about 50° C. for about 2 hours being suitable. Since the reaction speed is a function of the pH of the saturated aqueous solution, the reaction time can be varied by varying the pH from the optimum value disclosed above. The fluorescent material is preferably added to the intermediate product prior to carrying out this reaction, and in an amount that is in slight excess to approximately stoichiometric proportions. Although a larger excess could be used, no advantage would be obtained.

As the final essential step of this process, the fluorescent composition is recovered, washed and dried. Suitably, recovery is by filtration, with the resulting reaction slurry of the preceding essential step being advantageously filtered through a sintered glass filter funnel having a pore size smaller than the particle size. The fluorescent composition is recovered as a filter cake, and the filter cake is washed using a series of solvents to remove solvent-soluble impurities from the cake. An advantageous series of solvents comprises water, methanol, tetrahydrofuran, acetone and then methanol again. About one liter of each of these solvents per 10 grams of filter cake is suitably used for washing the filter cake. Finally, the filter cake is dried according to conventional procedures.

Methods of Use

The fluorescent composition of the present invention is useful for detecting radioactivity and for detecting a nonfluorescent species, such as phospholipids, when placed in a cell. This fluorescent composition is also useful in thin-layer chromatography (TLC) where, when coated on a suitable substrate, it acts as the chromatographic medium and permits detection of radioactive bands. In the disclosure that follows concerning these uses, the fluorescent composition is termed a bonded phase scintillator (BPS) and the fluorescent material is termed a scintillator.

In its broadest terms, the method of using the BPS for detecting radioactivity comprises placing a radioactive species in a cell packed with the BPS and then detecting the emitted radioactivity; provided that when the radioactivity being detected is that of tritiated hydrogen or carbon-14, the particle size of the BPS is about 5 to 10 microns. The radioactive species to be detected may be present, for example, in the effluent from a liquid chromatography column used to separate this species from impurities or from other radioactive species.

When tritiated hydrogen is being detected, it is necessary to use a BPS having a particle size no larger than about 5 to 10 microns because tritiated hydrogen is a soft $\beta$-emitter. A particle size of about 5 to 10 microns assures that the path length traversed by a beta particle through the solvent before contacting a BPS particle is small. When BPS particles are packed in a cell, the distance from one BPS particle to another is about $\frac{1}{3}$ of the diameter of an average size BPS particle. A particle size of about 5 to 10 microns thus results in an average beta particle path length through the solvent of only about 2 to 3 microns.

It is uncertain whether a beta particle must actually contact the BPS directly in order for scintillation energy transfer to occur. Possibly, the beta particle may indirectly transfer energy to the BPS by initially directly exciting the solvent molecules. In any event, the energy transfer is ultimately to the scintillator of the BPS. Inasmuch as dipole-dipole energy transfer probabilities are proportional to the inverse sixth power of the distance between the energy donator and the energy acceptor, energy transfer from the radioactive species directly to the scintillator of an adjacent BPS particle is quite efficient.

The cell in which the BPS is packed may be, e.g., a glass test tube suitable for use in a conventional scintillation counter, or a disposable cartridge, or a flow cell.

In a particular embodiment of the method of this invention, the BPS is packed in a glass test tube that is suitable for use in a conventional scintillation counter. The radioactive species is added to the packed test tube, and radioactivity is detected using a scintillation counter. Suitable glass test tubes are well known, with a Pyrex tube having either a 2 mm or 4 mm internal diameter being exemplary thereof. A standard Beckman scintillation counter can be used as the counter. This particular embodiment is illustrated by two examples, as set forth as below.

In a closely related embodiment, the BPS is prepacked as a dry powder in a disposable cartridge. The cartridge has a calibrated, unfilled void volume, represented by X, which enables one to take a radioactive sample in X ml of solvent and load it into the cartridge by syringe injection. The cartridge is then sealed and placed in a conventional scintillation counter.

In another embodiment of the method of this invention, the cell into which the BPS is packed is a flow cell. In this embodiment, the radioactive species is contained in the effluent from a liquid chromatography column, preferably a column used in a high-pressure liquid chromatography (HPLC) technique; and the effluent is passed through the flow cell. This embodiment has the advantage of permitting continuous radioactivity detection, and accordingly provides the capability for continuous radioactivity detection in HPLC.

In carrying out continuous radioactivity detection in HPLC, the effluent from a high-pressure liquid chromatography column is passed through a flow cell packed with the BPS, and the radioactivity of a radioactive species in the effluent is detected. Other details concerning this embodiment (e.g., the optimum column flow rate, the flow cell design, and radioactivity detection techniques) are known in the art, as exemplified by the above-cited publications of Clifford et al. and Sieswerda et al.

Use of the BPS of the present invention for detecting nonfluorescent species, such as phospholipids, involves a method similar to that described above for radioactivity detection, except that a different type of detection apparatus is required and the cell is irradiated with electromagnetic radiation of a frequency that causes the BPS to fluoresce. Thus, a cell packed with the BPS is irradiated and the emitted fluorescence is detected. The irradiation and detection are continued as the sample is placed in the cell; and the enhancement or reduction in intensity, or shift in frequency, of the emitted fluorescence caused by interaction between the non-fluorescent species and the BPS is detected.

In one embodiment of the method for detecting nonfluorescent species, the sample passes from a LC column, preferably a HPLC column, into a flow cell packed with BPS. Prior to the sample reaching the flow cell, the flow cell is irradiated with electromagnetic radiation of a frequency that causes the BPS to fluoresce, and the emitted fluorescence is detected. The irradiation and detection are continued as the sample passes into the flow cell, and the enhancement or reduction in intensity or shift in frequency due to interaction between the nonfluorescent species and the BPS is detected. Other details of this technique are known in the art, as disclosed in the article by P. Asmus et al. in *Journal of Chromatography*, Vol. 126, page 317 (1976).

Additionally, the BPS of the present invention is useful in thin-layer chromatography (TLC). For this use, the BPS is coated as a slurry onto a suitable substrate such as a plastic or glass plate, and is then dried. The type of coating procedure involved is conventional. The TLC plate is then used for chromatography in a conventional manner, with the BPS acting as the chromatographic medium during chromatography, and with the BPS subsequently permitting detection of radioactive bands using conventional detection equipment such as a scanner.

Specific examples of the present invention are set forth below. Unless otherwise indicated, all percentages are by weight. It is to be understood that these examples are merely illustrative and are in no way to be interpreted as limiting the scope of the invention.

EXAMPLE 1

A bonded phase scintillator (BPS) according to the present invention is prepared by the following process. To a slurry in distilled water of 10 grams of 10-micron Lichrosorb ® Si-60 (a microparticulate silica gel sold by Merck, Inc., which has a size of 10 microns), there is added 10 milliliters of N-2-aminoethyl-3-aminopropyl trimethoxysilane. The resulting slurry is stirred at room temperature for 3 hours. After the reaction is completed, the slurry is then filtered on a sintered glass filter funnel having a pore size smaller than 5 microns. There is recovered on the funnel as a filter cake an intermediate product consisting of the N-2-aminoethyl-3-aminopropyl silyl groups covalently chemically bonded to the silica gel. This intermediate product is N-2-aminoethyl-3-aminopropyl silica. The filter cake is washed with 250 milliliters of each of the following solvents, in turn: water, methanol, tetrayhdrofuran, and then methanol again. The washed filter cake is then dried. To a slurry of 10 grams of the intermediate product in 100 milliliters of a 4:1 mixture of acetonitrile and water saturated with sodium bicarbonate, there is added 1 gram of dansyl chloride, and the resulting slurry is heated at 50° C. for 2 hours. The slurry from this reaction is then filtered on a sintered glass filter funnel having a pore size smaller than 5 microns to recover didansyl-N-2-aminoethyl-3-aminopropyl silica (the BPS) as a filter cake. The filter cake is washed with 1 liter of each of the following solvents, in turn: water, methanol, tetrahydrofuran, acetone, and then methanol again. The BPS is then dried.

EXAMPLE 2

The BPS produced in Example 1 is packed into a Pyrex tube of 2 millimeter internal diameter; and the packed tube is then filled with $C^{14}$-benzoic acid in toluene having an activity of $4.7 \times 10^5$ DPM/ml and sold by New England Nuclear Corporation of Boston, Massachusetts. Using a standard Beckman scintillation counter, a 35% counting efficiency is determined.

EXAMPLE 3

Following the procedure of Example 2, a Pyrex tube of 4 millimeter internal diameter and packed with the BPS of Example 1 is filled with tritiated toluene in toluene having an activity of $2.5 \times 10^6$ DPM/ml and sold by New England Nuclear Corporation of Boston, Massachusetts. A counting efficiency of 1.7% is obtained.

Industrial Applicability

The fluorescent composition of the present invention is useful for detecting the radioactivity of a radioactive species, and for detecting a nonfluorescent species such as a phospholipid, when placed in a cell. Such a cell could be a test tube, a disposable cartridge, or a flow cell. Furthermore, the fluorescent composition is useful in thin-layer chromatography when coated on a suitable substrate such as glass.

I claim:

1. A process for the manufacture of a fluorescent composition comprising an inert porous particle having a size of about 5 to 20 microns, and a fluorescent material; said fluorescent material being fixedly attached by covalent chemical bonding to the surface of said particles; wherein said particle is microparticulate silica; said process comprising steps of:
    (a) reacting at room temperature an amine linking agent with an aqueous slurry of said silica whereby there is formed an intermediate product consisting of said amine linking agent covalently bonded to said silica;
    (b) recovering, washing and drying said intermediate product;
    (c) reacting at room temperature a slurry of the dried intermediate product with said fluorescent material whereby said fluorescent composition is produced; and
    (d) recovering, washing and drying said fluorescent composition.

2. The process of claim 1 wherein said silica is high pressure liquid chromatography grade silica gel.

3. The process of claim 1 wherein said particle has a size of about 5 to 10 microns.

4. The process of claim 1 wherein the reaction of step (a) is carried out at about room temperature for a period of about 2 to 4 hours.

5. The process of claim 4 wherein the reaction time is about 3 hours.

6. The process of claim 1 wherein the reaction of step (c) is carried out at a temperature in the range of about 40° to 60° C. for about 1 to 3 hours.

7. The process of claim 1 wherein the slurry of step (c) is produced by adding the dried intermediate product to a mixture of a water-miscible organic solvent and a saturated aqueous solution, said organic solvent being present in an excess amount or in an about stoichiometrically equivalent amount with respect to said aqueous solution.

8. The process of claim 7 wherein said organic solvent is present in an about 4:1 ratio with respect to said aqueous solution.

9. The process of claim 8 wherein said organic solvent is acetonitrile.

10. The process of claim 7 wherein said saturated aqueous solution is water saturated with sodium bicarbonate.

11. The process of claim 1 wherein the reaction of step (c) is carried out at about 50° C. for about 2 hours.

12. The process of claim 1 wherein the amine linking agent is N-2-aminoethyl-3-aminopropyl trimethoxysilane.

13. The process of claim 1 wherein the amine linking agent is an amine-containing trialkoxysilane.

14. The process of claim 1 wherein said fluorescent composition is didansyl-N-2-aminoethyl-3-aminopropyl silica.

15. The process of claim 1 wherein said fluorescent material is dansyl chloride.

16. A fluorescent composition useful for detection of radioactive or non-fluorescent species by fluorescence, said composition comprising microparticulate silica having a size of about 5 to 20 microns, an amine linking agent fixedly attached by covalent chemical bonding to the surface of said microparticulate silica by reacting said microparticulate silica with said amine linking agent to form an intermediate product, and a fluorescent material fixedly attached to said amine linking agent by reacting said fluorescent material with the said intermediate product, said microparticulate silica-amine linking agent reaction comprising (a) reacting at room temperature an amine linking agent with an aqueous slurry of said silica whereby there is formed an intermediate product consisting of said amine linking agent covalently bonded to said silica and (b) recovering, washing and drying said intermediate product, and said fluorescent material-intermediate product reaction comprising (c) reacting at about room temperature a slurry of the dried intermediate product with said fluorescent material whereby said fluorescent composition is produced, and (d) recovering, washing and drying said fluorescent composition.

17. The fluorescent composition of claim 16 wherein said silica is high-pressure liquid chromatography grade silica gel.

18. The fluorescent composition of claim 16 wherein said silica has a size of about 5 to 10 microns.

19. The fluorescent composition of claim 16 wherein said amine linking agent is N-2-aminoethyl-3-aminopropyl trimethoxysilane.

20. The fluorescent composition of claim 19 wherein said fluorescent material is dansyl chloride, and said fluorescent composition is didansyl-N-2-aminoethyl-3-aminopropyl silica.

21. The composition of claim 16 wherein the reaction of step (a) is carried out at about room temperature for a period of about 2 to 4 hours.

22. The composition of claim 21 wherein the reaction time is about 3 hours.

23. The composition of claim 16 wherein the slurry of step (c) is produced by adding the dried intermediate product to a mixture of a water-miscible organic solvent and a saturated aqueous solution, said organic solvent being present in an excess amount or in an about stoichiometrically equivalent amount with respect to said aqueous solution.

24. The composition of claim 23 wherein said organic solvent is present in an about 4:1 ratio with respect to said aqueous solution.

25. The composition of claim 24 wherein said organic solvent is acetonitrile.

26. The composition of claim 23 wherein said saturated aqueous solution is water saturated with sodium bicarbonate.

27. The composition of claim 16 wherein the reaction of step (c) is carried out at about 50° C. for about 2 hours.

* * * * *